United States Patent
Kross

[11] Patent Number: 6,123,966
[45] Date of Patent: Sep. 26, 2000

[54] STABILIZED TWO-PART DISINFECTING SYSTEM AND COMPOSITIONS AND METHODS RELATED THERETO

[75] Inventor: Robert D. Kross, Bellmore, N.Y.

[73] Assignee: Alcide Corporation, Redmond, Wash.

[21] Appl. No.: 09/146,595

[22] Filed: Sep. 3, 1998

[51] Int. Cl.[7] ........................ A01N 59/00; A01N 37/00; A01N 37/04; A61K 33/20; A61K 31/19; A61K 31/194; A61L 2/16

[52] U.S. Cl. ........................ 424/665; 424/601; 424/605; 424/606; 424/661; 424/666; 424/703; 424/709; 424/713; 424/718; 514/41; 514/143; 514/557; 514/574; 514/709; 514/710; 514/711; 514/944; 514/970; 422/29; 422/37; 210/764; 504/151; 252/187.21; 252/187.23

[58] Field of Search ...................... 424/665, 601, 424/605, 606, 661, 666, 703, 709, 713, 718; 514/141, 143, 557, 574, 709–711, 944, 970; 504/151; 422/29, 37; 210/764; 252/187.21, 187.23

[56] References Cited

U.S. PATENT DOCUMENTS

| | | | |
|---|---|---|---|
| Re. 31,779 | 12/1984 | Alliger | 422/28 |
| Re. 36,064 | 1/1999 | Davidson et al. | 424/665 |
| 3,983,214 | 9/1976 | Misato et al. | 514/53 |
| 4,104,190 | 8/1978 | Hartshorn | 252/187.21 |
| 4,199,564 | 4/1980 | Silver et al. | 514/358 |
| 4,258,056 | 3/1981 | Lentsch | 514/566 |
| 4,376,787 | 3/1983 | Lentsch et al. | 514/576 |
| 4,891,216 | 1/1990 | Kross et al. | 424/661 |
| 4,942,177 | 7/1990 | Kastendieck | 514/560 |
| 4,945,110 | 7/1990 | Brokken et al. | 514/517 |
| 4,986,990 | 1/1991 | Davidson et al. | 424/665 |
| 5,100,652 | 3/1992 | Kross | 424/53 |
| 5,384,134 | 1/1995 | Kross et al. | 424/661 |
| 5,389,390 | 2/1995 | Kross | 426/332 |
| 5,651,996 | 7/1997 | Roozdar | 424/665 |
| 5,696,046 | 12/1997 | Green | 502/161 |
| 5,820,822 | 10/1998 | Kross | 422/37 |

FOREIGN PATENT DOCUMENTS

| | | |
|---|---|---|
| 287 074 | 10/1988 | European Pat. Off. . |
| 530861 | 3/1993 | European Pat. Off. . |
| WO 96/18300 | 6/1996 | WIPO . |
| WO 97/09054 | 3/1997 | WIPO . |
| WO 99/16418 | 4/1999 | WIPO . |

OTHER PUBLICATIONS

Chemical Abstracts 125: 177473 (1996), Database STNonline.
CAB Abstract 96: 42517 (1995), Database STNonline.
CAB Abstract 81: 17628 (1978), Database STNonline.
VETU Abstract 1984–62285 (1984), Database STNonline.
CAB Abstract 84: 110318 (1984), Database STNonline.
CAB Abstract 82: 22513 (1982), Database STNonline.

*Primary Examiner*—John Pak
*Attorney, Agent, or Firm*—Seed Intellectual Property Law Group PLLC

[57] ABSTRACT

A stabilized two-part disinfecting system comprising a first part and a second part adapted to be mixed to yield an aqueous disinfecting composition. The first part contains a non-esterifying acid and an alcohol-containing humectant or antifreeze, while the second part contains a salt of an organic acid and an optional metal chlorite. Methods for making a disinfecting composition by mixing the two-part disinfecting system, as well as for disinfecting substrates by contact therewith, are also disclosed.

56 Claims, No Drawings

STABILIZED TWO-PART DISINFECTING SYSTEM AND COMPOSITIONS AND METHODS RELATED THERETO

TECHNICAL FIELD

The present invention relates to a stabilized two-part disinfecting system, as well as a disinfecting composition and method for making and using the same, and more particularly, to a two-part disinfecting system having a first part containing a non-esterifying acid and an alcohol-containing humectant or antifreeze, and a second part containing a salt of an antimicrobial organic acid and an optional metal chlorite.

BACKGROUND OF THE INVENTION

Topical germicides often contain harsh chemical components which can adversely affect the quality of the skin. The resulting irritation is exacerbated by the presence of materials, such as surface active agents and the germicides themselves, which can disrupt and even dissolve protective skin lipids. The disruption of the lipid barrier of the skin leads to moisture loss and subsequent irritation and cracking. Skin is particularly susceptible to damage under adverse ambient conditions, such as occurs in windy, wet and cold weather, when chapping most often occurs. Irritated, chapped and cracked skin tissue can readily harbor pathogenic bacteria, including those that cause mammalian mastitis. Sore mammalian teats are particularly sensitive to the attachment of the milking claws, which often limits the ability of dairymen to milk the affected quarter.

To reduce the potential for chapping, cracking and related skin irritations, many topical disinfectants, including most current teat dips, include humectants. Humectants are agents that control the moisture exchange between the applied skin and the environment. Typical humectants that are used in teat dips are glycerin and sorbitol, and which contain multiple hydroxyl groups ("polyols"). Such humectants attract water, and when present on skin maintain a higher-than-normal level of moisture. Furthermore, teat tips may also contain relatively higher levels of polyols, such as propylene glycol, to serve as antifreeze agents. Polyols, at their ordinary levels of use in teat dips, of up to about 10% of the disinfecting composition, are relatively inert with respect to other teat dip components, tending to esterify with organic acid germicides at low, and acceptable rates. However, as polyol levels increase, the esterification tendency escalates markedly. The ester formation involves the primary alcohol (i.e., —$CH_2OH$) of the polyol.

This tendency to esterify is particularly burdensome when preparing teat dip concentrates, which products are finding increased utility and economy in modern dairy farms. Teat dip concentrates require less bulk shipping and handling, and occupy less space in dairy barns and milking parlors. They are combined with water on site, often by means of equipment which dilutes and sprays the dip in a single operation. Dip concentrates containing germicidal organic acids at levels up to about 20%, are particularly susceptible to such esterification reactions, leading to the reduction of both germicidal and humectant functionality.

A particular area in which polyol esterification is a source of difficulty is in the two-part chlorous acid germicides, wherein an acidified chlorous acid disinfectant is generally formed by combining an activator containing an organic acid with a base containing a metal chlorite. In these two-part systems, the polyol must be combined with the organic acid in the activator because of its instability in the base. A critical aspect of chlorous acid germicides is the need to maintain their pH values in a range where the chlorous acid/chlorite ratio is below about 0.18, so that excessive degradation to chlorine dioxide does not occur. This generally requires the presence of an organic acid buffering system, comprising an acid in pK range of about 2.8 to about 4.2. Concentrates of these two-part organic acid/chlorite systems which also contain polyols in the acid phase are even more difficult to maintain in stable form.

Accordingly, there is a need in the art for improved two-part systems which can stably maintain alcohol-containing humectants or antifreezes with germicidal organic acids, or acid activators for chlorite systems, over an extended period of time. This invention fulfills this need, and provides further related advantages.

SUMMARY OF THE INVENTION

In brief, the present invention provides a stabilized two-part disinfecting system comprising a first part and a second part adapted to be mixed to yield an aqueous disinfecting composition, wherein the first part contains a non-esterifying acid and an alcohol-containing humectant or antifreeze, and the second part contains an anion of an antimicrobial organic acid and an optional metal chlorite. The phrase "an anion of an antimicrobial organic acid" is also referred to herein as "a salt of an organic acid." In one embodiment, the salt of the organic acid of the second part is an antimicrobial organic acid anion which, upon combination with the first part, is at least partially converted to its protonated form. The protonated form of the organic acid is the active, antimicrobial form of the organic acid. In another embodiment, the second part further comprises a metal chlorite. In this embodiment, the salt of the organic acid, upon combination with the first part, is at least partially converted to its active, protonated form, while the metal chlorite concomitantly reacts with the non-esterifying acid to yield an antimicrobial chlorous acid germicide.

The first and second parts may both be in the form of an aqueous solution, cream or gel, or one or both may be in solid form with the other part having been pre-mixed with water. For example, the first and second parts may be aqueous solution or gels to be mixed in approximately equal volumes to form the disinfecting composition, or may be concentrates to be diluted by water and then mixed to yield the disinfecting composition. Alternatively, the first and/or second parts may be in solid form or liquid form to be mixed prior to dilution with water or upon addition thereto. In the embodiment where the second part contains a metal chlorite, care should be taken to avoid excessive generation of chlorine dioxide upon mixing. This may be avoided, for example, by mixing the first and second parts only after initial dilution with water.

The non-esterifying acid is present in the first part such that, upon combination with the second part, at least 50%, generally at least 70% and typically 90%, of the salt of the organic acid is converted to its corresponding acid form, and the pH of the disinfecting composition is reduced to below about 5.0. In terms of pH, the non-esterifying acid is present in the first part such that the resulting disinfecting composition has a pH ranging from 2.3, generally from 2.5 and typically from 2.7, up to about 5.0.

The alcohol-containing humectant or antifreeze is present in the first part such that it, when combined with the second part, is present within the disinfecting composition at a concentration ranging from 2–40% by weight, generally from 3–25% and typically from 5–15% by weight. In one embodiment, the alcohol-containing humectant or antifreeze is a polyhydric humectant or antifreeze and, in more specific embodiments, is glycerin or sorbitol. To this end, it should be understood that the alcohol-containing humectant or antifreeze may be both a humectant and an antifreeze, and that the term "or" in this context does not mean that the terms "humectant" and "antifreeze" are mutually exclusive. In other words, a suitable alcohol-containing component can function as either a humectant or antifreeze, or as both a humectant and antifreeze.

The salt of the organic acid is present in the second part at a concentration such that it, when combined with the first part, is present within the disinfecting composition at a concentration ranging from about 0.25–10% by weight, generally from 0.5–5% and typically from 1–3% by weight. Representative salts of organic acids include sodium or potassium lactate, mandelate, citrate and malate.

When the second part further comprises a metal chlorite, the metal chlorite is present in the second part such that, when combined with the first part, it is present within the disinfecting composition at a concentration ranging from 0.005–1% by weight, generally from 0.05–0.5% and typically from 0.1–0.4% by weight. Suitable metal chlorites are water-soluble chlorites, including alkali or alkaline earth chlorites, such as sodium or potassium chlorite. In this embodiment, a base is also present in the second part in an amount sufficient to adjust the pH of the second part to a value ranging from about 9 to about 11.5, and typically from 10.5 to 11. Suitable bases in this regard include alkali metal hydroxides such as sodium, potassium or lithium hydroxide.

One or both of the first and second parts may further comprise optional components such as textural modifiers, wetting agents, thickening agents, film-forming polymers, colorants, preservatives, and mixtures thereof. Such optional components are present in either the first or second parts, or both parts, such that when the first and second parts are combined the resulting disinfecting composition has the desired amounts and/or characteristics attributable to such optional components.

In another aspect of this invention, a method is disclosed for making a disinfecting composition by mixing the two-part disinfecting system of this invention. Further methods include disinfection of a substrate by contacting the substrate with a disinfecting composition made by combination of the two-part disinfecting system of this invention. In this context, the substrate may be any surface in need of such disinfection, including (but not limited to) skin or tissue in general, as well as body fluids and mucosal membranes. In a specific application, the substrate is the teat of a dairy cow.

These and other aspects of this invention will be evident upon reference to the following detailed description of the invention.

DETAILED DESCRIPTION OF THE INVENTION

Organic acids and alcohols, when present in a suitable medium, will interact to form esters, through elimination of a molecule of water, as illustrated by the following reaction (1):

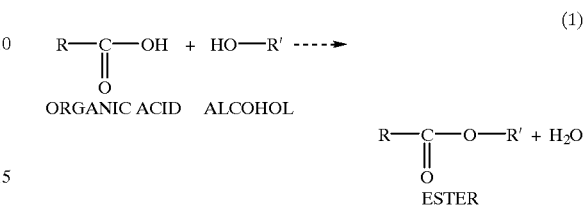

where R and R' are the same or different organic moieties. When R' contains one or more additional OH groups (the molecule being termed a "polyol"), the most reactive OH groups are primary (1°) alcohols—that is, an alcohol bound to a 1° carbon. For example, a 1° alcohol will preferentially react with an organic acid to form the corresponding ester as illustrated in the following reaction (2):

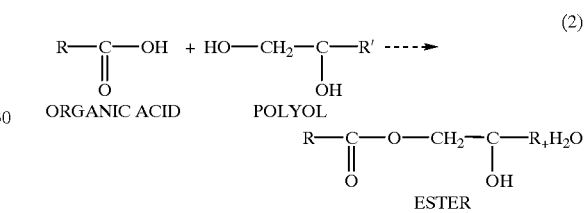

In certain topical formulations, it is desirable to combine alcohol-containing compounds with organic acids, which serve either as antimicrobial agents or as proton donors that can activate antimicrobial agents, or both. The alcohol-containing compounds can serve as skin-conditioning humectants, or freeze-resistant (i.e., "antifreeze") components of aqueous formulations, or both, in the topical formulation. However, upon continued contact, such as in a commercial package of the product for two or more years, the organic acid will slowly esterify and thereby be diminished in its amount and effectiveness. Reduction in the level of intact humectant or antifreeze will also result.

In the practice of the present invention, the organic acid is employed in the second part of a two-part system as the salt of the organic acid. Such salts can be readily formed by, for example, combination of the organic acid with sodium hydroxide to form the sodium salt of the organic acid as illustrated by scheme (3).

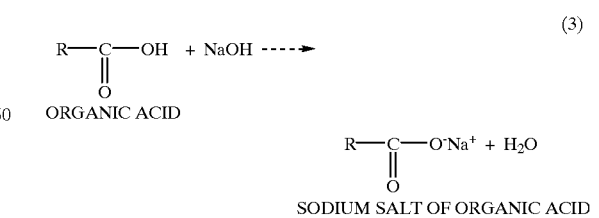

One skilled in the art would readily recognize that alkalis with numerous cations may be employed to generate salts of organic acids, including (in addition to sodium) potassium, lithium and quaternary ammonium salts. Such salts, when present in aqueous medium, exist when the pH is in excess of about 7.

In one embodiment, the second part further comprises a metal chlorite. Upon acidification, both the salt of the organic acid and the metal chlorite will convert to their corresponding acid forms, to a degree depending upon the quantity of hydrogen ion available. A non-esterifying acid is provided in the first or "activator" part of the two-part system, along with the alcohol-containing humectant or antifreeze. The non-esterifying acid has an inherent strength significantly greater than that of the non-ionized organic acid, or acids, which exist(s) in ionized form in the base part of the system, so that the combination of the two parts creates an effective amount of unionized organic acid.

Upon mixture of the two parts, the hydrogen ions provided to the composition by the non-esterifying acid will interact with the organic acid anions, converting them at least in part to their non-ionized form. The relative amount of non-ionized organic acid that is formed, with respect to total anion initially present, will depend upon the final pH of the mixed composition. Many organic acids function as antimicrobial agents because of the ability of their non-ionized forms to migrate across microbial cell walls and disrupt the internal acid/base balance of the cells, whereas their anionic forms cannot.

In the practice of this invention, the relative amount of the non-ionized form of the organic acid must be at least about 10% of the total organic acid present in both non-ionized and ionized forms. In addition, in the embodiment where the second part further comprises is a metal chlorite, the relative amount of chlorous acid which is formed upon combination of the first and second parts must be no more than about 25% of the total chlorite that exists in both non-ionized and ionized forms in the combined composition. The resulting disinfecting composition, therefore, comprises non-ionized organic acids present minimally at about 10% of the total organic acid pool, and chlorous acid present maximally at about 25% of the total chlorite pool. Thus, when utilized in the embodiment where the second part contains a metal chlorite, the composition has the advantage of rapid, high-level disinfection derived from both the chlorous acid that is formed, but which degrades rapidly, as well as the organic acids which can remain active for a longer period of time but which possess lower inherent antimicrobial activity.

The antimicrobial organic acids whose anions or salts may be used in this invention in the second part of the two-part disinfecting system of this invention, individually or in combination include, but are not limited to, such small molecule acids as formic, acetic and propionic acids, as well as members of the group of α-hydroxy carboxylic acids having a pKa from 2.8 to 4.2 such as glycolic, lactic, malic, mandelic, citric and tartaric acids. Other, weaker acids that may be used include benzoic, caprylic, capric and the hydroxybenzoic acids. Salts of organic acids include potassium, sodium and quaternary ammonium salts. Preferred salts of organic acids include sodium or potassium lactate, mandelate, citrate or malate. The amount of the salt of the organic acid in the second part is such that, upon mixing with the first part, it yields a disinfecting composition containing the salt of the organic acid at a concentration ranging from about 0.25% to about 10%, generally from 0.5% to 5% and typically from 1% to 3%.

The non-esterifying acids of the first part which may be used in the practice of this invention, individually or in combination include, but are not limited to, inorganic acids such as sulfuric acid, sodium hydrogen sulfate, phosphoric acid, sodium dihydrogen phosphate, and nitric acid. Organic sulfonates and phosphonates may also serve in this capacity. The non-esterifying acid is present in the first part such that, when combined with the second part, it yields a disinfecting composition wherein at least 50% of the salt of the organic acid is converted to its corresponding acid form, generally at least 70% and typically at least 90%. With regard to pH, the amount of non-esterifying acid is sufficient to reduce the pH of the disinfecting composition to a level below about 5.0, and generally values from a lower limit of 2.3 to 2.5, or typically 2.7, up to 5.0.

Alcohol-containing humectants or antifreezes of the first part of this invention include monohydroxy and polyhydroxy alcohols, and certain alkyl ethers of the latter. This component is present in the first part in an amount such that, when combined with the second part, gives a disinfecting composition containing the humectant or antifreeze at a concentration ranging from about 2% to 40% by weight, generally from 3% to 25% and typically from 5% to 15% by weight. Representative monohydroxy alcohols are ethyl alcohol, n-propanol and isopropanol, and representative polyhydroxy alcohols or alkyl ethers thereof are glycerin, sorbitol, 1,2- and 1,3-propylene glycol, dipropylene glycol, alkyl ethers of dipropylene glycols, other sugar alcohols, and mixtures thereof. Preferred humectants are glycerin and sorbitol, which may be employed at a level of from about 0.5% to about 20% by weight, and more preferably from about 2% to about 10% by weight of the disinfecting composition.

Various optional ingredients may be included in either a single or both parts of the two-part system. Such ingredients include (but are not limited to) wetting agents, textural modifiers, film-forming polymers and colorants. The wetting agents facilitate contact of the composition with the skin, and can be selected from those materials recognized to provide this effect, in both identity and amount. Textural modifiers are those material which primarily affect the body of the mixed composition in terms of retention, flow and lubricity. These include thickening agents such as alkyl celluloses, alkoxy celluloses, xanthan gum, guar gum, and polyacrylamide derivatives, of which the polymer of 2-acrylamido-2-methylpropane sulfonic acid is a preferred example. Other textural modifiers include lanolin derivatives, acyl lactylates, polyethylene glycol, glyceryl esters, and mixtures thereof. Film-forming polymers include the above-referenced polyacrylamides, as well as the class of poly(vinyl alcohols/vinyl acetates) and polyvinyl pyrollidone. Colorants are generally selected from the group found acceptable for use in skin-contacting formulations, and are known to those skilled in the art.

In one embodiment of this invention, the concentration of the non-esterifying acid and the alcohol-containing humectant or antifreeze in the first part are from about 0.002% to about 1.0% by weight for the non-esterifying acid, and about 4% to about 80% for the alcohol-containing humectant or antifreeze.

In another embodiment, the second part further comprises a metal chlorite and the concentrations of the salt of the organic acid and the metal chlorite in the second part are from about 0.5% to about 20% by weight for the salt of the organic acid, and from about 0.01% to about 2% by weight for the metal chlorite.

In a further aspect of this invention, this invention is directed to a method for making a disinfecting composition comprising mixing the first part and the second part of the two-part disinfecting composition. In one embodiment, both the first and second parts are aqueous solutions, creams or gels. In another embodiment, at least one of the first or second parts is in a concentrated form, and the concentrated form (either solid or liquid) is mixed with the other part and then diluted with water, or diluted with water and then mixed with the other part.

In still another embodiment, a method for disinfecting a substrate is disclosed, wherein the method comprises contacting the substrate with an effective amount of a disinfecting composition formed by mixing the two-part disinfecting system of this invention. Suitable substrates include the skin or tissue of a warm-blooded animal and, in a preferred embodiment, is the teat of a dairy cow.

The following examples describe illustrative two-part disinfecting systems comprising both organic acid germicides and alcohol-containing humectants or antifreezes, as well as systems comprising organic acid germicides, alcohol-containing humectants or antifreezes and chlorous acid/chlorite antimicrobials, that are intended for the application to mammalian skin in accordance with this invention. It is to be understood that these examples are provided by way of illustration only, and nothing therein should be taken as a limitation upon the overall scope of the invention. All parts and percentages in the examples as well as the specification and claims are by weight.

EXAMPLE 1

This example illustrates the preparation of a mammalian teat dip in which an α-hydroxy carboxylic organic acid, lactic acid, is generated in an aqueous composition containing 10% glycerin as a topical humectant. The two-part system has a first part containing an inorganic acid and glycerin, and a second part containing an anion of an organic acid and a metal chlorite. The two-part formulations are as follows:

| | % w/w |
|---|---|
| Part 1 | |
| Phosphoric acid (86% tech.) | 5.81 |
| Glycerin | 20.00 |
| Sodium benzoate | 0.02 |
| Triton X-100 | 0.15 |
| FD&C Yellow #5 | 0.15 |
| Water | q.s. |
| Part 2 | |
| Sodium lactate | 5.13 |
| Sodium chlorite | 1.00 |

-continued

| | % w/w |
|---|---|
| Sodium hydroxide | q.s. to pH 10.5–11.00 |
| Water | q.s. |

Upon 1:1 combination, the pH of the resulting disinfecting composition is between 2.5 and 2.8. An appropriate adjustment in the amount of phosphoric acid in Part 1 is made if needed. Such an adjustment may be required if the sodium chlorite, which is ordinarily of a technical grade material, has an atypical level of alkali or carbonate impurities which require neutralization. This two-part system yields a chlorous acid disinfecting composition containing residual lactic acid germicide, as well as a high level of glycerin humectant. This formulation would not have been stable is both lactic acid and glycerin were present in a single phase. An additional advantage of this composition is that little noxious and destabilizing chlorine dioxide is generated immediately upon mixture of the two parts.

EXAMPLE 2

This example illustrates the preparation of two-part concentrate from which a lactic acid/humectant-containing germicidal teat dip is prepared by dilution with water. The second part contains the organic acid anion and a metal chlorite, and the first part an inorganic acid and glycerin, such that diluting each part with four parts of water, followed by subsequent combination, creates the germicidal and skin-protecting composition. The formulations are as follows:

| | % w/w |
|---|---|
| Part 1 | |
| Phosphoric acid (86% tech.) | 18.60 |
| Glycerin | 50.00 |
| Sodium benzoate | 0.02 |
| Triton X-100 | 0.75 |
| FD&C Yellow #5 | 0.75 |
| Xanthan Gum | 0.75 |
| Water | q.s. |
| Part 2 | |
| Sodium lactate | 16.42 |
| Sodium chlorite | 3.20 |
| Sodium hydroxide | q.s. to pH 10.5–11.00 |
| Water | q.s. |

Following dilution of each part, the pH of the subsequent 1:1 mixture is between 2.5 and 2.8. Again, for the reason noted above in Example 1, an appropriate adjustment in the amount of phosphoric acid may be made to Part 1 if needed.

EXAMPLE 3

This example illustrates the preparation of a freeze-resistant, thickened, film-forming two-part germicidal skin composition with a high level of humectancy comprising three antimicrobial organic acids which are regenerated by bisulfate and sulfonate acids. The formulation are as follows:

|  | % w/w |
| --- | --- |
| Part 1 | |
| Propylene glycol | 67.00 |
| Polyacrylamide methanesulfonic acid solution (16% solids; v = 300,000 cps) | 10.00 |
| Sodium acid sulfate | 9.00 |
| FD&C Blue #1 | 0.05 |
| Pluronic L-31 | 0.10 |
| Water | q.s. |
| Part 2 | |
| Benzoic acid | 0.40 |
| Propionic acid | 4.00 |
| Mandelic acid | 4.00 |
| Sodium Hydroxide | 3.35 |
| Water | q.s. |

Part 1 is prepared by dissolving the polysulfonic acid in the propylene glycol, and then adding the water, sodium acid sulfate, surfactant and colorant. Part 2 is prepared by first dissolving the sodium hydroxide in the required amount of water and then sequentially adding each acid, in order to convert them to their corresponding anion. The 1:1 combination of the two-part system provides a disinfecting composition that resists freezing to below 0° F., has high humectancy and film-forming capacity, and in which over 10% of the non-esterifying acid is supplied by the sulfonic acid polymer.

EXAMPLE 4

This example illustrates the preparation of a two-part thickened, freeze-resistant organic acid germicide with sorbitol humectant. The formulations are as follows:

|  | % w/w |
| --- | --- |
| Part 1 | |
| Sodium dihydrogen phosphate | 3.65 |
| Sorbitol (70% solution) | 25.00 |
| Natrosol 250 MR, hydroxyethyl cellulose | 0.60 |
| Triton X-100 | 0.35 |
| FD&C Red #33 | 0.02 |
| Water | q.s. |
| Part 2 | |
| Capric acid | 1.00 |
| Caprylic acid | 1.00 |
| Sodium Hydroxide | 0.52 |
| Water | q.s. |

Part 1 is prepared by dispersing the Natrosol in the sorbitol and then adding water, phosphate, Triton and colorant. Part 2 is prepared by first dissolving the sodium hydroxide in the required amount of water, and then sequentially adding each acid to convert them to their corresponding anion. The 1:1 germicidal combination has a thickened texture and provides excellent emolliency.

EXAMPLE 5

This example illustrates the preparation of an acidic concentrate part of a two-part organic acid/glycerin/metal chlorite teat dip which is formed upon 10-fold aqueous dilution of each part, and subsequent admixture. In this composition citric acid is directly combined with high levels of glycerin.

|  | % w/w |
| --- | --- |
| Citric acid | 11.80 |
| Glycerin | 40.00 |
| Poloxamine 1107 | 2.20 |
| Sodium benzoate | 0.18 |
| FD&C Yellow #5 | 3.30 |
| Water | q.s. |

Portions of this formulation were stored for 18 months at ambient temperatures, as well as at 40° C. for 1 week, and upon analysis provided the results set forth in Table 1. Because of instability (e.g., 27% loss of citric acid after 18 months), this formulation cannot be considered to be commercially viable.

TABLE 1

Citric Acid Concentrations, and Loss

|  |  | 1 week at 40° C. |  | 18 Months at Ambient |  |
| --- | --- | --- | --- | --- | --- |
| Time 0 |  | Concentration | Loss | Concentration | Loss |
| 11.82% |  | 11.28% | 4.7% | 8.63% | 27.0% |

The above formulation was prepared using 3.21% phosphoric acid (pure basis) in place of the citric acid (a lesser quantity is needed because of the greater acid strength of phosphoric than citric). Portions of this formulation were stored for 18 months at ambient temperatures, and at 40° C. for 1 week, and upon analysis provided the results set forth in Table 2. Because of greater stability (i.e., no significant loss after 18 months), this formulation can be considered to be commercially viable as an activator for the two-part system of this invention.

TABLE 2

Phosphoric Acid Concentrations, and Loss

|  |  | 1 week at 40° C. |  | 18 Months at Ambient |  |
| --- | --- | --- | --- | --- | --- |
| Time 0 |  | Concentration | Loss | Concentration | Loss |
| 3.21% |  | 3.18% | 0.9% | 3.05% | 4.9% |

From the foregoing it will be appreciated that, although specific embodiments of the invention have been described herein for purposes of illustration, various modifications may be made without deviating from the spirit ad scope of the invention. Accordingly, the invention is not limited except as by the appended claims.

What is claimed is:

1. A stabilized two-part disinfecting system comprising a first part and a second part adapted to be mixed to yield an aqueous disinfecting composition, wherein:

the first part comprises a non-esterifying inorganic acid, or a non-esterifying organic acid selected from the group consisting of organic sulphonic acid and organic phosphonic acid, or a mixture thereof, and an alcohol-containing humectant or antifreeze selected from the group consisting of a monohydroxy alcohol, a polyhydroxy alcohol, an alkyl ether of polyhydroxy alcohol and mixtures thereof; and the second part comprises a salt of an organic carboxylic acid, a metal chlorite and a base, wherein the base is present in the second part at a concentration sufficient to adjust the pH of the second part to a value ranging from about 9.0 to 11.5;

and wherein the non-esterifying inorganic acid or non-esterifying organic acid is present in the first part at a concentration so that, when combined with the second part, it is sufficient to convert at least 50% of the salt of the organic carboxylic acid to its corresponding acid form and to reduce the pH of the disinfecting composition to a level below about 5.0;

the alcohol-containing humectant or antifreeze is present in the first part at a concentration so that, when combined with the second part, it is present within the disinfecting composition at a concentration ranging from about 2% to about 40% by weight;

the salt of the organic carboxylic acid is present in the second part at a concentration so that, when combined with the first part, it is present within the disinfecting composition at a concentration ranging from about 0.25% to about 10% by weight; and the metal chlorite is present in the second part at a concentration so that, when combined with the first part, it is present within the disinfecting composition at a concentration ranging from about 0.005% to about 1% by weight.

2. The system of claim 1 wherein the metal chlorite is an alkali or alkaline earth chlorite.

3. The system of claim 1 wherein the metal chlorite is sodium chlorite or potassium chlorite.

4. The system of claim 1 wherein the metal chlorite is sodium chlorite.

5. The system of claim 1 wherein the metal chlorite is present in the second part at a concentration so that, when combined with the first part, it is present within the disinfecting composition at a concentration ranging from 0.05% to 0.5% by weight.

6. The system of claim 1 wherein the metal chlorite is present in the second part at a concentration so that, when combined with the first part, it is present within the disinfecting composition at an concentration ranging from 0.1% to 0.4% by weight.

7. The system of claim 1 wherein the base is present in the second part at a concentration sufficient to adjust the pH of the second part to a value ranging from 10.5 to 11.0.

8. The system of claim 1 wherein the base is an alkali metal hydroxide.

9. The system of claim 8 wherein the alkali metal hydroxide is sodium potassium or lithium hydroxide.

10. The system of claim 8 wherein the base is sodium hydroxide.

11. The system of claim 1 wherein the salt of the organic carboxylic acid is a salt of an alpha-hydroxy carboxylic acid.

12. The system of claim 11 wherein the alpha-hydroxy carboxylic acid has a pK ranging from 2.8 to 4.2.

13. The system of claim 11 wherein the alpha-hydroxy carboxylic acid is glycolic, lactic, malic, mandelic, citric, tartaric, or mixtures thereof.

14. The system of claim 11 wherein the alpha-hydroxy carboxylic acid is lactic acid.

15. The system of claim 1 wherein the salt of the organic carboxylic acid is a potassium, sodium or quarternary ammonium salt.

16. The system of claim 1 wherein the salt of the organic carboxylic acid is sodium or potassium lactate, mandelate, citrate or malate.

17. The system of claim 1 wherein the salt of the organic carboxylic acid is sodium lactate.

18. The system of claim 1 wherein the salt of the organic carboxylic acid is present in the second part at a concentration so that, when combined with the first part, it is present within the disinfecting composition at a concentration ranging from 0.5% to 5.0% by weight.

19. The system of claim 1 wherein the salt of the organic carboxylic acid is present in the second part at a concentration so that, when combined with the first part, it is present within the disinfecting composition at an concentration ranging from 1.0% to 3.0% by weight.

20. The system of claim 1 wherein the non-esterifying inorganic acid is sulfuric, phosphoric, hydrochloric, nitric, or mixtures thereof.

21. The system of claim 20 wherein the non-esterifying inorganic acid is phosphoric acid.

22. The system of claim 20 wherein the non-esterifying inorganic acid is sodium acid sulfate or sodium dihydrogen phosphate.

23. The system of claim 1 wherein the non-esterifying organic acid is an alkyl or aryl sulfonic acid or an alkyl or aryl phosphonic acid.

24. The system of claim 1 wherein the non-esterifying inorganic or non-esterifying organic acid is present in the first part at a concentration so that, when combined with the second part, it is sufficient to convert at least 70% of the salt of the organic carboxylic acid to its corresponding acid form.

25. The system of claim 1 wherein the non-esterifying inorganic or non-esterifying organic acid is present in the first part at a concentration so that, when combined with the second part, it is sufficient to convert at least 90% of the salt of the organic carboxylic acid to its corresponding acid form.

26. The system of claim 1 wherein the non-esterifying inorganic acid or non-esterifying organic acid is present in the first part at a concentration so that, when combined with the second part, it is sufficient to lower the pH of the disinfecting composition to a value from about 2.3 to about 5.0.

27. The system of claim 1 wherein the non-esterifying inorganic acid or non-esterifying organic acid is present in the first part at a concentration so that, when combined with the second part, it is sufficient to lower the pH of the disinfecting composition to a value from 2.5 to about 5.0.

28. The system of claim 1 wherein the non-esterifying inorganic acid or non-esterifying organic acid is present in the first part at a concentration so that, when combined with the second part, it is sufficient to lower the pH of the disinfecting composition to a value from 2.7 to about 5.0.

29. The system of claim 1 wherein the alcohol-containing humectant or antifreeze is the monohydroxy alcohol.

30. The system of claim 29 wherein the monohydroxy alcohol is ethyl alcohol, n-propanol or isopropanol.

31. The system of claim 1 wherein the alcohol-containing humectant or antifreeze is the polyhydroxy alcohol or the alkyl ether thereof.

32. The system of claim 31 wherein the polyhydroxy alcohol or the alkyl ether thereof is glycerin, sorbitol, 1,2-propylene glycol, 1,3-propylene glycol, dipropylene glycol, alkyl ethers of dipropylene glycol, or mixtures thereof.

33. The system of claim 1 wherein the alcohol-containing humectant or antifreeze is the alcohol-containing humectant.

34. The system of claim 33 wherein the alcohol-containing humectant is glycerin or sorbitol.

35. The system of claim 1 wherein the alcohol-containing humectant or antifreeze is the alcohol-containing antifreeze.

36. The system of claim 35 wherein the alcohol-containing antifreeze is a propylene glycol.

37. The system of claim 1 wherein the alcohol-containing humectant or antifreeze is present in the first part at a concentration so that, when combined with the second part, it is present within the disinfecting composition at a concentration ranging from 3% to 25% by weight.

38. The system of claim 1 wherein the alcohol-containing humectant or antifreeze is present in the first part at a concentration so that, when combined with the second part, it is present within the disinfecting composition at an concentration ranging from 5% to 15% by weight.

39. The system of claim 1 wherein the first part and the second part are adapted to be mixed in about equal volumes.

40. The system of claim 1 wherein the first and the second part are adapted to be mixed at a volume ratio of 1:1.

41. The system of claim 1 wherein the concentrations of the non-esterifying inorganic and/or non-esterifying organic acid and the alcohol-containing humectant or antifreeze in the first part are from about 0.002% to about 1.0% by weight for the non-esterifying inorganic acid or non-esterifying organic acid, and about 4% to about 80% for the alcohol-containing humectant or antifreeze.

42. The system of claim 39 wherein the concentrations of the salt of the organic carboxylic acid and the metal chlorite in the second part are from about 0.5% to about 20% by weight for the salt of the organic carboxylic acid, and from about 0.01% to about 2% by weight for the metal chlorite.

43. The system of claim 1 wherein the first part is an aqueous solution, cream or gel.

44. The system of claim 1 wherein the second part is an aqueous solution, cream or gel.

45. The system of claim 1 wherein at least one of the first part or the second part is in solid or non-aqueous liquid form.

46. The system of claim 1 wherein the disinfecting composition further comprises a textural modifier, wetting agent, thickening agent, film-forming polymer, colorant, preservative, or mixture thereof.

47. A disinfecting composition formed by mixing the first part and the second part of the two-part disinfecting composition of claim 1.

48. A method for making a disinfecting composition comprising mixing the first part and the second part of the two-part disinfecting composition of claim 1.

49. The method of claim 48 wherein both the first part and the second part are in the form of an aqueous solution, cream or gel.

50. The method of claim 48 wherein at least one of the first part or second part is in a concentrated form.

51. The method of claim 50 wherein the concentrated from is mixed with water prior to mixing with the other component.

52. The method of claim 50 wherein the concentrated form is mixed with the other component, and then diluted with water.

53. The method of claim 48 wherein at least one of the first part or second part is in the form of a solid or non-aqueous liquid.

54. A method for disinfecting a substrate comprising contacting the substrate with an effective amount of a disinfecting composition formed by mixing the two-part disinfecting system of claim 1.

55. The method of claim 54 wherein the substrate is skin or tissue of a warm-blooded animal.

56. The method of claim 54 wherein the substrate is a teat of a dairy cow.

* * * * *

UNITED STATES PATENT AND TRADEMARK OFFICE
CERTIFICATE OF CORRECTION

PATENT NO. : 6,123,966
DATED : September 26, 2000
INVENTOR(S) : Robert D. Kross

It is certified that error appears in the above-identified patent and that said Letters Patent is hereby corrected as shown below:

Column 11,
Line 57 "is sodium potassium or" should read -- is sodium, potassium or --.

Column 13,
Line 36, "system of claim 1, wherein" should read -- system of claim 39 wherein --.

Signed and Sealed this

Twenty-fifth Day of December, 2001

*Attest:*

JAMES E. ROGAN
*Attesting Officer*   *Director of the United States Patent and Trademark Office*